United States Patent
Accisano, III et al.

(10) Patent No.: US 11,717,319 B2
(45) Date of Patent: Aug. 8, 2023

(54) DRAINAGE CATHETER EXCHANGE SYSTEM AND ASSOCIATED METHODS

(71) Applicant: Merit Medical Systems, Inc., South Jordan, UT (US)

(72) Inventors: Nicholas Accisano, III, Howell, NJ (US); Christopher A. Heine, Schwenksville, PA (US)

(73) Assignee: Merit Medical Systems, Inc., South Jordan, UT (US)

( * ) Notice: Subject to any disclaimer, the term of this patent is extended or adjusted under 35 U.S.C. 154(b) by 28 days.

(21) Appl. No.: 16/869,342

(22) Filed: May 7, 2020

(65) Prior Publication Data

US 2020/0352594 A1 Nov. 12, 2020

Related U.S. Application Data (60) Provisional application No. 62/846,180, filed on May 10, 2019.

(51) Int. Cl.
*A61B 17/34* (2006.01)

(52) U.S. Cl.
CPC ...... *A61B 17/3421* (2013.01); *A61B 17/3415* (2013.01); *A61B 17/3468* (2013.01); *A61B 2017/347* (2013.01); *A61B 2017/3456* (2013.01); *A61B 2017/3458* (2013.01)

(58) Field of Classification Search
CPC .......... A61B 17/32053; A61B 17/3415; A61B 17/3421; A61B 17/3468; A61B 17/32075; A61B 17/320708; A61B 17/320783; A61B 2017/3458; A61B 2017/347; A61B 2017/320791; A61B 2017/00477; A61B 1/00112; A61M 25/0054; A61M 25/0133; A61M 25/0662; A61M 2025/0163; (Continued)

(56) References Cited

U.S. PATENT DOCUMENTS

| | | | |
|---|---|---|---|
| 2,242,831 | A | 5/1941 | McIntosh |
| 2,876,496 | A | 3/1959 | Murphy, Jr. |
| 3,094,124 | A | 6/1963 | Birtwell |

(Continued)

FOREIGN PATENT DOCUMENTS

| | | |
|---|---|---|
| EP | 0109657 | 5/1984 |
| EP | 2392437 | 12/2011 |
| WO | 2014159431 | 10/2014 |

OTHER PUBLICATIONS

International Search Report and Written Opinion dated Aug. 24, 2020 for PCT/US2020/031911.

(Continued)

*Primary Examiner* — Jocelin C Tanner
(74) *Attorney, Agent, or Firm* — Dorsey & Whitney LLC (57) ABSTRACT

Catheter exchange systems and methods may use a cutting tool to sever an encrusted catheter. The cutting tool may include a flexible cannula to encompass and move along the encrusted catheter. A sheath may selectively cover the cutting tool. The cutting tool may selectively transition between a first position in which the cutter is within the sheath and a second position in which the cutting tool is extended beyond the sheath to sever a suture of the catheter. A locking stylet may be used to secure the position of the encrusted catheter and remove the encrusted catheter.

12 Claims, 10 Drawing Sheets

(58) Field of Classification Search
CPC .. A61F 2002/30431; A61F 2002/30429; A61F 2002/30426; A61F 2002/30329
See application file for complete search history.

(56) References Cited

U.S. PATENT DOCUMENTS

| | | | |
|---|---|---|---|
| 4,068,515 A | 1/1978 | Kowal et al. | |
| 4,256,106 A | 3/1981 | Shoor | |
| 4,264,294 A | 4/1981 | Ruiz | |
| 4,402,136 A | 9/1983 | Rast | |
| 4,430,081 A | 2/1984 | Timmermans | |
| 4,535,616 A | 8/1985 | Eason | |
| 4,625,464 A | 12/1986 | Kubo | |
| 4,813,260 A | 3/1989 | Strybel | |
| 4,837,931 A | 6/1989 | Beermann | |
| 5,020,221 A | 6/1991 | Nelson | |
| 5,221,263 A | 6/1993 | Sinko et al. | |
| 5,267,966 A | 12/1993 | Paul | |
| 5,283,951 A | 2/1994 | Davenport et al. | |
| 5,308,318 A | 5/1994 | Plassche, Jr. | |
| 5,380,304 A | 1/1995 | Parker | |
| D372,782 S | 8/1996 | Spehalski | |
| 5,645,539 A | 7/1997 | Solomon et al. | |
| 5,651,781 A | 7/1997 | Grace | |
| 6,496,561 B1* | 12/2002 | Meyer | A61N 5/1001 378/65 |
| 6,994,009 B2 | 2/2006 | Carter | |
| 7,182,746 B2 | 2/2007 | Haarala et al. | |
| 7,318,334 B2 | 1/2008 | Carter | |
| 7,641,630 B2 | 1/2010 | Accisano, III et al. | |
| 7,740,616 B2 | 6/2010 | Smith et al. | |
| 7,938,809 B2 | 5/2011 | Lampropoulos et al. | |
| 8,177,771 B2 | 5/2012 | Butts et al. | |
| 2002/0010416 A1 | 1/2002 | Uflacker | |
| 2003/0217624 A1 | 11/2003 | Dittmar | |
| 2004/0040796 A1 | 3/2004 | Pham | |
| 2004/0054377 A1* | 3/2004 | Foster | A61B 10/04 606/167 |
| 2004/0133124 A1* | 7/2004 | Bates | A61B 10/0275 600/564 |
| 2004/0171997 A1 | 9/2004 | Wilson et al. | |
| 2005/0149060 A1* | 7/2005 | Thorstenson | A61M 25/0668 606/108 |
| 2005/0159676 A1* | 7/2005 | Taylor | A61B 17/3403 600/567 |
| 2005/0182435 A1 | 8/2005 | Andrews et al. | |
| 2005/0192537 A1 | 9/2005 | Osborne et al. | |
| 2005/0261664 A1* | 11/2005 | Rome | A61M 25/0097 604/167.03 |
| 2006/0137973 A1 | 6/2006 | Herrington | |
| 2006/0167417 A1 | 7/2006 | Kratz et al. | |
| 2006/0235431 A1 | 10/2006 | Goode et al. | |
| 2006/0276773 A1 | 12/2006 | Wilson et al. | |
| 2007/0016167 A1 | 1/2007 | Smith et al. | |
| 2007/0175048 A1 | 8/2007 | Holley et al. | |
| 2008/0236358 A1 | 10/2008 | Vitullo et al. | |
| 2009/0158597 A1 | 6/2009 | Braga et al. | |
| 2009/0326560 A1 | 12/2009 | Lampropoulos et al. | |
| 2010/0031793 A1 | 2/2010 | Hayner et al. | |
| 2010/0317996 A1* | 12/2010 | Dillon | A61B 10/0266 600/567 |
| 2010/0331823 A1 | 12/2010 | Blanchard | |
| 2011/0190734 A1* | 8/2011 | Graffam | A61M 25/04 604/540 |
| 2012/0016192 A1* | 1/2012 | Jansen | A61B 1/00154 600/104 |
| 2012/0065543 A1* | 3/2012 | Ireland | A61B 10/0275 600/567 |
| 2012/0095475 A1 | 4/2012 | Barmada | |
| 2012/0253295 A1 | 10/2012 | Nentwick et al. | |
| 2013/0282059 A1 | 10/2013 | Ketai et al. | |
| 2015/0258313 A1* | 9/2015 | Seaver | A61M 25/0194 604/8 |
| 2015/0342580 A1* | 12/2015 | Clancy | A61B 10/04 600/567 |
| 2016/0106405 A1* | 4/2016 | Merk | A61B 17/00234 606/108 |
| 2016/0303349 A1* | 10/2016 | Braga | A61M 25/0102 |
| 2016/0331945 A1* | 11/2016 | Shah | A61M 25/0102 |
| 2016/0361080 A1 | 12/2016 | Grace et al. | |
| 2016/0361088 A1* | 12/2016 | Maguire | A61F 2/95 |

OTHER PUBLICATIONS

International Search Report and Written Opinion dated Dec. 19, 2013 for PCT/US2013/062685.
Notice of Allowance dated Jul. 23, 2015 for U.S. Appl. No. 14/041,833.
Office action dated Mar. 24, 2015 for U.S. Appl. No. 14/041,833.
Extended European Search Report dated Dec. 21, 2022 for EP208055467.

* cited by examiner

DRAINAGE CATHETER EXCHANGE SYSTEM AND ASSOCIATED METHODS

RELATED APPLICATIONS

This application claims priority to U.S. Provisional Application No. 62/846,180, filed on May 10, 2019 and titled "Drainage Catheter Exchange System and Associated Methods" which is hereby incorporated by reference in its entirety.

TECHNICAL FIELD

The present disclosure relates to medical instruments and systems for removing and exchanging catheters. More particularly, some embodiments relate to removal of drainage catheters comprising a suture.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Drainage catheters are used in a variety of medical settings for draining fluids from a patient's body. For example, a patient may suffer an injury or have a medical problem where a bodily tissue retains an excess amount of fluid, such as blood or other bodily serum. If the fluid is not removed further complications in the patient can occur such as rupturing or infection of the tissue. Accordingly, drainage catheters may be placed to remove these fluids from the patient, to either relieve pressure or otherwise reduce fluid build-up.

In some embodiments, drainage catheters may comprise a hub, an elongate catheter tube in fluid communication with the hub, and a distal portion that includes a plurality of drainage bores. The drainage bores may be configured to allow communication of fluid from the patient's body through the elongate catheter tube. Some drainage catheters further include a suture disposed within a portion of the drainage lumen extending along a portion of the length of the catheter. The suture may be attached or secured to the tip of the catheter to facilitate deflecting the catheter tip away from a straight configuration into a curved or pig-tail configuration to anchor the catheter within a patient. For example, the practitioner may insert the catheter tube into a patient's body in a straight configuration, then pull on the suture to form a curved loop at the distal end to anchor the catheter within the patient's body.

To remove the catheter, the suture may be released to allow the catheter to return from a pig-tail configuration to a straight configuration. However, in some instances, the suture may become encrusted, which, in turn, may case the catheter to become stuck in a pig-tail configuration. Removing a catheter while in the pig-tail configuration may cause discomfort and/or injury. Described herein are systems, methods, and devices that may be used to remove a catheter even when a suture has become encrusted.

For example, in some embodiments, a drainage catheter exchange system may comprise a sheath, a cutter, and a locking stylet. The locking stylet may be used to hold the catheter in place while the sheath and cutter are slid along the catheter. The sheath may cover the cutter as the sheath and cutter are advanced along the catheter. The cutter may be advanced out of the sheath to sever the suture. After the suture is severed, the catheter may more readily returned to a straight configuration and may be withdrawn from the patient.

In addition to removing a catheter, embodiments described herein may be used to place a new catheter. In some embodiments, a physician may leave the sheath in the patient after a catheter has been removed, and subsequently use the sheath to insert a new catheter. Thus, the sheath may also serve as an introducer.

Embodiments of the disclosure may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrase "coupled to" is broad enough to refer to any suitable coupling or other form of interaction between two or more entities, including mechanical and fluidic interaction. Thus, two components may be coupled to each other even though they are not in direct contact with each other. The phrases "attached to" and "attached directly to" refer to interaction between two or more entities that are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use. With specific application to a drainage catheter exchange system, the proximal end refers to the end that a physician may handle when inserted in a patient, while the distal end is configured for insertion into a patient when in use.

As used herein, the term "suture" is broad enough to include filaments, tethers, wires, cords, straps, or other elongated flexible members configured to deflect a catheter, or maintain the shape of a catheter, when tension is applied to the suture.

Figure 1:
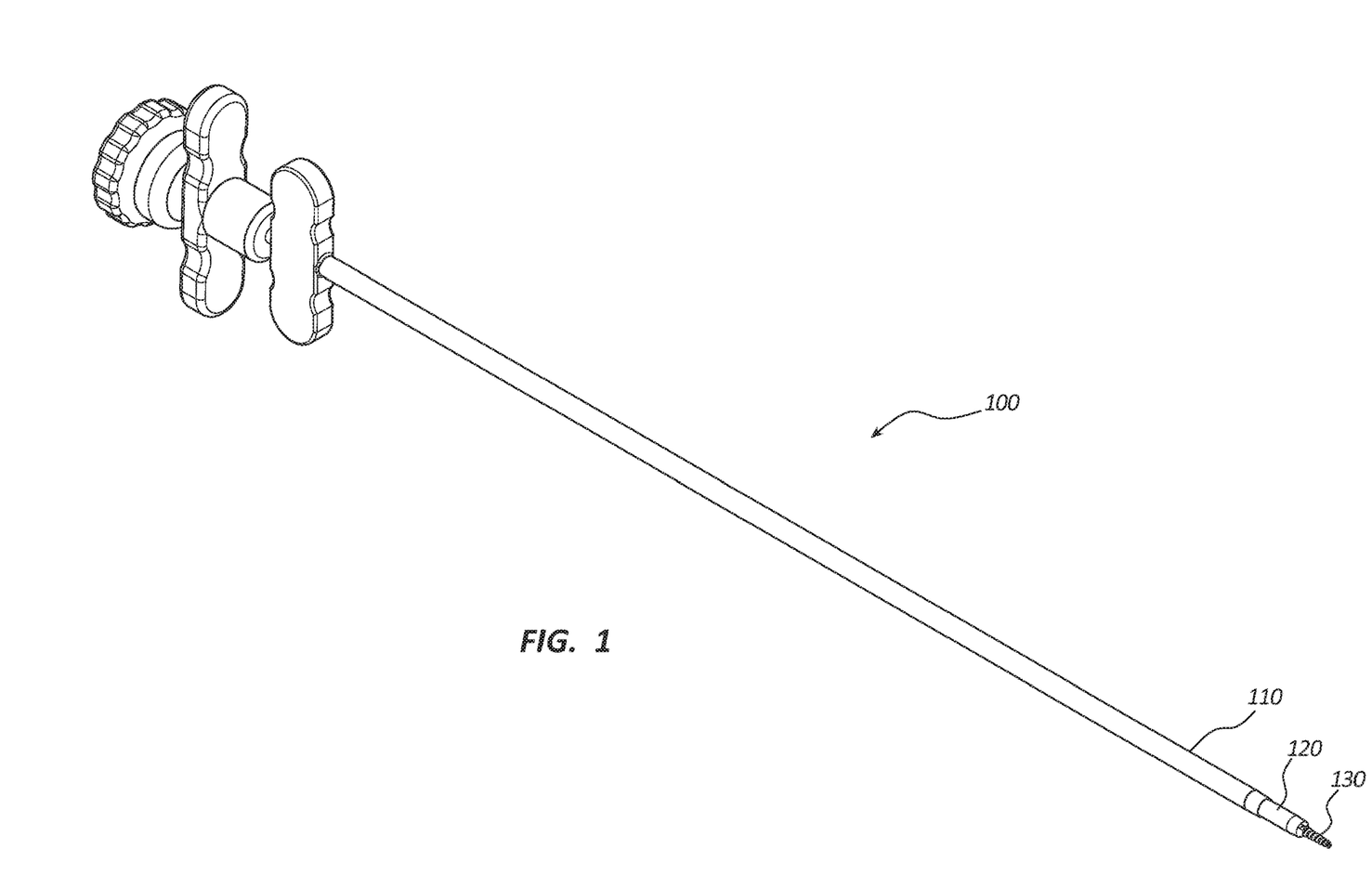
FIG. 1 is a perspective view of a drainage catheter exchange system, according to one embodiment.

FIG. 1 is a perspective view of a drainage catheter exchange system 100, according to one embodiment. The illustrated drainage catheter exchange system 100 comprises a locking stylet 130, a cutting tool 120, and a sheath 110. In some embodiments, the drainage catheter exchange system 100 may also comprise a replacement catheter.

The locking stylet 130 selectively couples to a catheter. More specifically, a distal portion of the locking stylet 130 is configured to selectively couple to a proximal portion of a catheter. In some embodiments, the locking stylet 130 engages the outer diameter of the proximal portion of the catheter. In some embodiments, the locking stylet 130 engages the inner diameter of the proximal portion of the catheter. Other locations and types of coupling between the locking stylet 130 and a catheter are also within the scope of this disclosure. Furthermore, in some instances, prior to coupling the locking stylet 130 to a catheter, a practitioner may cut or otherwise remove a hub from the catheter. In embodiments where the catheter has a proximal hub, removal of the hub may facilitate coupling of the locking stylet 130 directly to an elongate tube of the catheter.

The locking stylet 130 may assist with catheter movement during a procedure to remove or replace a catheter. With the locking stylet 130 coupled to a catheter, a physician may grasp a proximal portion of the locking stylet 130 to stabilize or secure the catheter, which may minimize undesired catheter movement (e.g., the catheter being pushed further into a patient by the cutting tool 120 and the sheath 110). For example, the locking stylet 130 may be used by a physician to secure the placement of the catheter while the cutting tool 120 and the sheath 110 advance along the catheter. Additionally, after the suture is severed, the locking stylet 130 may provide the physician with a grip that extends beyond the sheath 110 to remove the catheter without removing the sheath 110, thereby allowing the sheath to be used to introduce a replacement catheter. Further, the locking stylet 130 may function as a guide for placing the cutting tool 120 and the sheath 110 over the catheter.

The cutting tool 120 may be configured to sever a suture securing a catheter in a pig-tail configuration. The cutting tool 120 may be a cylindrical device that can encompass and slide along the locking stylet 130 and the catheter. In some embodiments, the cutting tool 120 may be a separate component from the sheath 110. In other embodiments, the cutting tool 120 may be integrated into the sheath 110. For example, the sheath 110 may have a sharpened edge.

In some embodiments, the sheath 110 is placed over the cutting tool 120 to provide a guard for the cutting tool 120. The cutting tool 120 may be longer than the sheath 110 and be able to slide longitudinally relative to the sheath 110, such that the distal portion of the cutting tool 120 may be disposed within, or exposed by, the sheath 110 based on the position of the cutting tool 120 relative to the sheath 110. While the cutting tool 120 is within the sheath 110, the sheath 110 may minimize or prevent the cutting tool 120 from causing trauma to the patient while the cutting tool 120 and sheath 110 advance along the catheter. For example, the sheath 110 may cover the cutting tool 120 such that the cutting tool 120 does not cut into tissue as the cutting tool 120 is advanced over the catheter.

Figure 2:
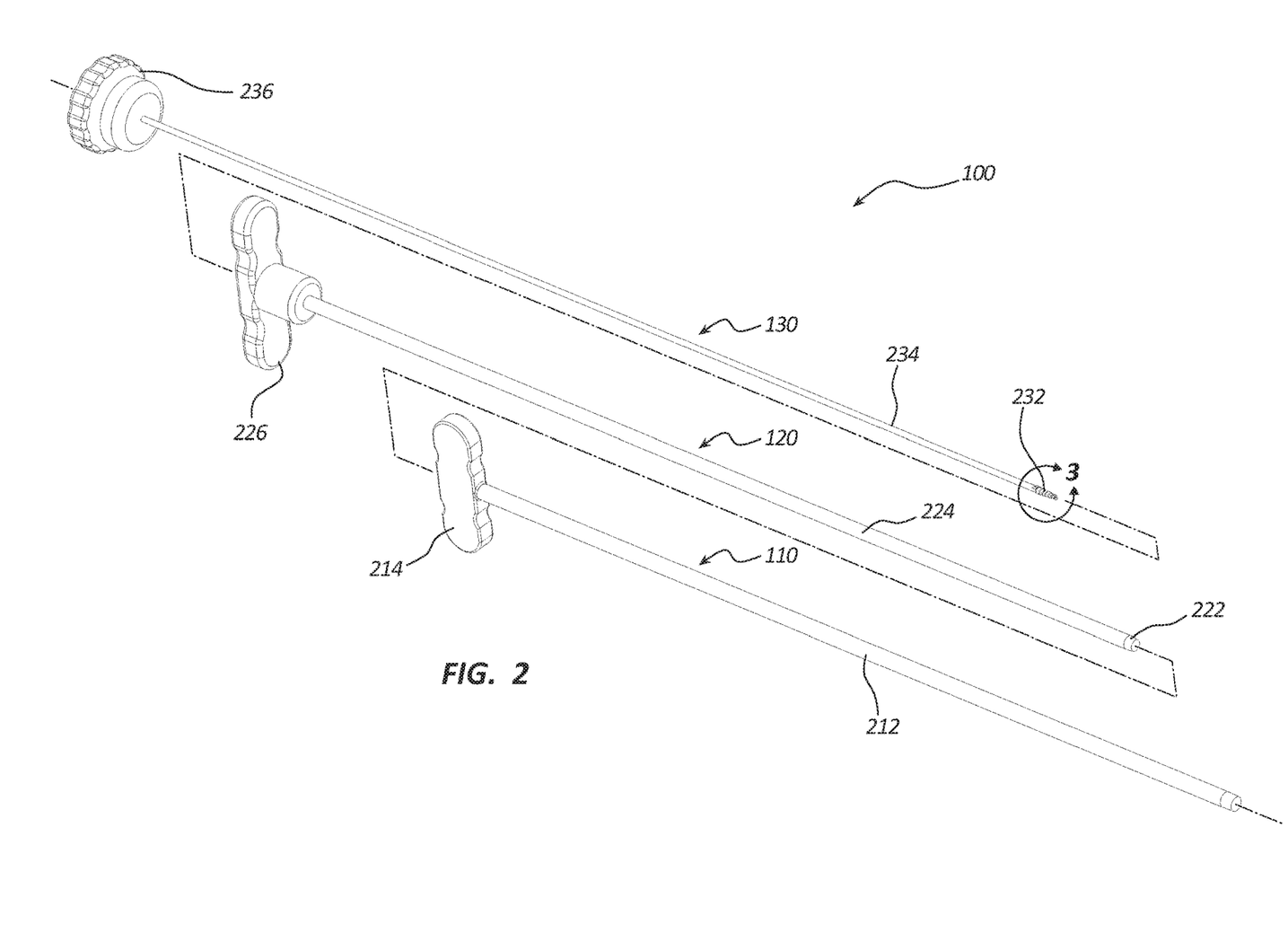
FIG. 2 is an exploded view of the drainage catheter exchange system of FIG. 1.

FIG. 2 is an exploded view of the drainage catheter exchange system 100 of FIG. 1. The drainage catheter exchange system 100 comprises the locking stylet 130, the cutting tool 120, and the sheath 110. The locking stylet 130 is configured to be nested in the cutting tool 120, and the cutting tool 120 is configured to be nested in the sheath 110. Stated another way, the locking stylet 130 may be configured to be disposed within a lumen of the cutting tool 120 and the cutting tool 120 may be configured to be disposed within a lumen of the sheath 110.

The sheath 110 may comprise a handle 214 and a shaft 212. In some embodiments, the shaft 212 is flexible. The flexibility of the shaft 212 may facilitates movement along a catheter even if the catheter is bent or curved. The handle 214 provides a grip for a physician to advance or retract the sheath 110 along the catheter. In some embodiments, the sheath 110 is splittable, to allow the sheath 110 to be removed from around a replacement catheter comprising a hub (as further discussed below).

In the illustrated embodiment, the cutting tool 120 comprises a cannula with a flexible shaft 224 and a cutter 222. The cutting tool 120 is configured to surround a catheter. The sheath 110 may be positioned around at least a portion of the cutting tool 120. For instance, the sheath 110 may cover the cutter 222 while the cutting tool 120 and the sheath 110 are advanced along a catheter to a suture of the catheter. The sheath 110 includes an aperture at the distal end of the flexible shaft 224, and at least a portion of the cutting tool 120 may be selectively extended through the aperture.

In the illustrated embodiment, the cutter 222 is at a distal end of the flexible shaft 224. Again, the cutter 222 may selectively transition between a first position in which the cutter 222 is within the sheath 110 and a second position in which the cutter 222 is extended beyond the sheath 110. In some embodiments, the cutter 222 comprises a circular cutting blade at the distal end of the cutting tool 120. For example, the circular cutting blade may be a sharpened edge around a circumference of the distal end of the flexible shaft 224. In some embodiments, the cutter 222 comprises a series of serrations. In some embodiments, the cutter 222 comprises a series of notches, including embodiments wherein each of the notches comprises a blunt distal tip and an angled portion that is sharpened. By blunting the distal tip of the notches, the cutter 222 may be configured to avoid cutting the patient when the cutter 222 is extended from the sheath 110.

As shown, in some embodiments, the cutter 222 may include a handle 226. The handle 226 provides a grip for a physician to advance or retract the cutting tool 120 along a catheter. Additionally, the physician may use the handle 226 to move the cutting tool 120 longitudinally in relation to the sheath 110 to expose the cutter 222 or sheath the cutter 222.

In some embodiments, the cutting tool 120 may selectively lock into a position relative to the sheath 110. For example, the cutting tool 120 may be locked into a sheathed position where the cutter 222 is within the sheath 110. In some embodiments, a physician may exert a deliberate force (e.g., a longitudinal force or a rotational force) to remove the cutting tool 120 from a locked position.

In some embodiments, the sheath 110 may prevent the cutting tool 120 from extending past a target distance. For example, the handle 214 of the sheath 110 limits the longitudinal position of the handle 226 of the cutting tool 120. As the handle 226 of the cutting tool 120 may not advance through the handle 214 of the sheath, the cutter 222 is limited in its distance to advance beyond the sheath 110. Thus, the length of the flexible shaft 224 of the cutting tool 120 in relation to the length of the shaft 212 of the sheath 110 may determine the distance that the cutter 222 may advance beyond the sheath 110.

In some embodiments, the sheath 110 may be used to sever a suture of a catheter. For example, a cutting portion may be integrated into the sheath 110. The sheath 110 may have a sharpened edge, serrations, or notches with a blunt distal tip and sharpened interior edges. In these embodiments, the cutting tool 120 may not be included in the drainage catheter exchange system 100.

Embodiments where the drainage catheter exchange system 100 does not include a cutter 222, cutting tool 120, or cutting portion of the sheath 110 are also within the scope of this disclosure. Without a cutting mechanism the drainage catheter exchange system 100 could still be used to exchange a catheter. The locking stylet 130 may be used to secure the old catheter while the sheath 110 is placed and to remove the old catheter through the sheath 110. The sheath 110 could be left in place and serve as an introducer for a new catheter. Such systems may be used when the suture is released from the hub (such as when the suture is not encrusted) or the sheath 110 may be pushed against the suture to displace or break the suture without the use of a cutting portion.

In the illustrated embodiment, the locking stylet 130 comprises a shaft 234, a locking mechanism 232, and a handle 236. The locking mechanism 232 is at a distal portion of the shaft 234, and the handle 236 is at a proximal end of the shaft 234.

The locking mechanism 232 couples the distal portion of the shaft 234 of the locking stylet 130 to a proximal portion of a catheter. For example, a physician may remove a hub of a catheter and use the locking mechanism 232 to couple the locking stylet 130 to the inner diameter or outer diameter of the catheter. The locking mechanism 232 may include one or more of a screw thread, fingers, or barbs.

In the illustrated embodiment, the locking mechanism 232 may comprise a screw thread to secure the locking stylet 130 to the catheter. The handle 236 of the locking stylet 130 may be used to apply a rotational force to the locking mechanism 232. The rotational force can cause the screw thread to engage an inner surface of the catheter when the locking mechanism 232 is inserted into a proximal opening of the catheter.

The locking stylet 130 may be configured to be used on a variety of catheters of different sizes. For example, catheters may range from 6 French (Fr) to 16 Fr. In some embodiments, the locking stylet 130 may be sized for a specific catheter size. In some embodiments, the locking stylet 130 could couple to a range of sizes of catheters. For example, the locking mechanism 232 in the illustrated embodiment has a conical shape. The conical shape may have a tip with a diameter sized for a 6 Fr size catheter and widen to a diameter sized for a 9 Fr size catheter, for example.

In some embodiments, the locking stylet 130 may include a lumen. The lumen would allow the locking stylet 130 to be placed over a guidewire, including a guidewire previously disposed within the catheter.

In some embodiments, the locking stylet 130 may not include the handle 236. Without the handle 236, the sheath 110 and the cutting tool 120 may be placed over the locking stylet 130 after the locking stylet 130 has been coupled to the catheter. In some embodiments, the locking stylet 130 may be tapered on one or both ends.

Figure 3:
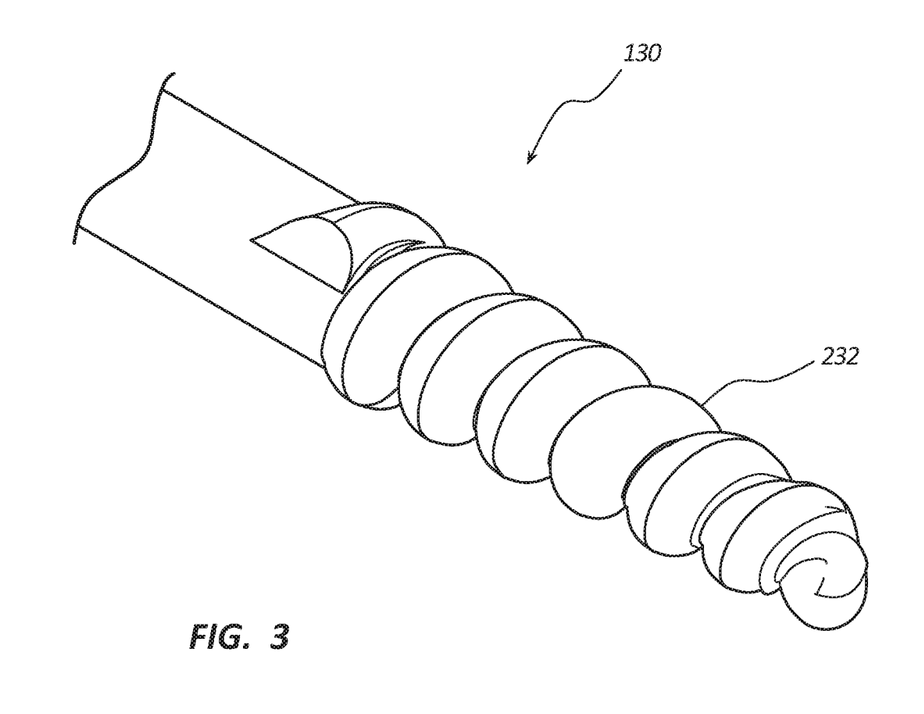
FIG. 3 is a detail view of a locking mechanism of a locking stylet of the drainage catheter exchange system of FIG. 1.

FIG. 3 is a detail view of the locking mechanism 232 of the locking stylet 130 of the drainage catheter exchange system 100 of FIG. 1. In the illustrated embodiment, the locking mechanism 232 comprises a helical thread around a conical tip.

The helical thread is configured to engage an inner surface of a catheter when the conical tip is inserted into a proximal opening of the catheter and rotated. The rotated locking mechanism 232 may form a friction fit with the inner surface of the catheter. A physician may rotate the locking stylet 130 in an opposite direction (opposite the rotational direction used to couple the locking mechanism 232 to the catheter) to release the locking mechanism 232 from the catheter. The helical thread may be rounded to prevent tearing the catheter.

In some embodiments, the conical tip can couple to a drainage catheter with a range of sizes. The conical tip tapers out from the vertex of the tip. The conical tip features a diameter that progressively expands as the tip tapers away from the vertex of the tip. Thus, a smaller drainage catheter may be secured with the first and second revolutions of the helical thread, while a larger drainage catheter may be secured with the last several revolutions of the helical thread. For example, a conical tip may be tapered to fit a catheter with a size between 9 Fr and 12 Fr.

In some embodiments, the conical tip may not be configured to taper to couple to a range of catheter sizes. The conical tip may still comprise a taper, but the tip geometry may be configured to couple to a single catheter size. In such embodiments, the physician selects an appropriate-sized locking stylet 130 for the drainage catheter. A kit may include multiple locking stylets to accommodate different-sized catheters.

Figure 4:
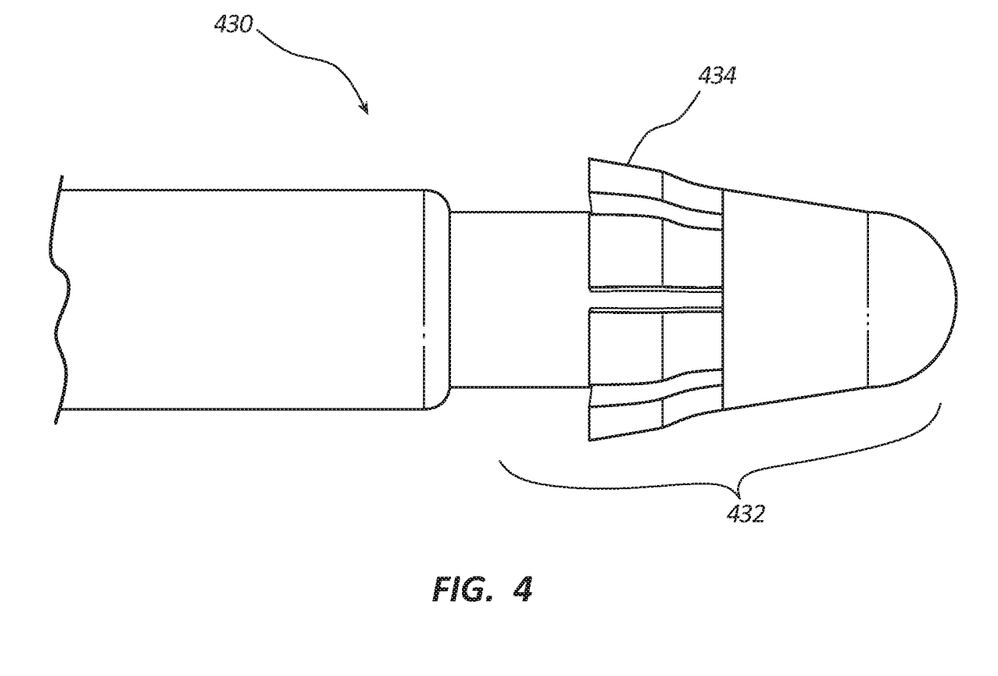
FIG. 4 is detail view of a locking mechanism of a locking stylet, according to a second embodiment.

FIG. 4 is detail view of a locking mechanism 432 of a locking stylet 430, according to a second embodiment. The locking mechanism 432 comprises a plurality of barbs 434 (which may also be referred to as push-in fingers) to engage an inner surface of the catheter when the locking stylet 430 is inserted into a proximal opening of the catheter.

The plurality of barbs 434 are positioned around a distal portion of the locking stylet 430. Each of the plurality of barbs 434 extends proximally and away from a center of the locking stylet 430. Because the plurality of barbs 434 are sloped away from the distal end of the locking stylet 430, the locking mechanism 432 may be configured to be inserted into a proximal opening of the catheter without catching on an edge of the catheter.

Each of the plurality of barbs 434 is connected to the locking stylet 430 along a single edge. Each of the plurality of barbs 434 may be able to flex inward toward the center of the locking stylet 430. When the plurality of barbs 434 are deflected inward, they may exert an outward spring force.

When the locking mechanism 432 is inserted into a proximal opening of the catheter with a longitudinal force, the inner surface of the catheter deflects the plurality of barbs 434 inwardly. The plurality of barbs 434 may exert an outward spring force, causing the plurality of barbs 434 to engage with the inner surface of the catheter. The spring force may secure the locking mechanism 432 within the catheter.

The plurality of barbs 434 may be formed in a variety of ways. In some embodiments, the plurality of barbs 434 may be formed from the distal portion of the locking stylet 430. For example, a portion of the locking stylet 430 may be removed to form integrated barbs. In other embodiments, a cap comprising the plurality of barbs 434 may be coupled to the distal portion of the locking stylet 430.

In the illustrated embodiment, the diameter of the distal portion of the locking stylet 430 is smaller than the diameter of the proximal portion of the locking stylet 430. The smaller diameter of the distal portion provides space for the plurality of barbs 434 to flex inwardly toward the center of the locking stylet 430.

In some embodiments, the locking mechanism 432 can couple to a drainage catheter with a range of sizes. The plurality of barbs 434 may flair out from the center of the locking stylet 430. The outward extension of the plurality of barbs 434 may allow the locking mechanism 432 to couple to multiple diameters of catheter or may be configured to couple to a specific diameter catheter. In embodiments configured to couple to a variety of catheter sizes, a smaller diameter catheter would cause the plurality of barbs 434 to flex inwardly more than a larger diameter catheter; however, the spring force exerted by the plurality of barbs 434 on the larger diameter catheter may still be sufficient to couple the locking stylet 430 to the catheter.

In some embodiments, the plurality of barbs 434 are not configured to deflect to couple to a range of catheter sizes. In these embodiments, the physician selects an appropriate-sized locking stylet 130. A kit may include multiple locking stylets to accommodate different catheter sizes.

Figure 5:
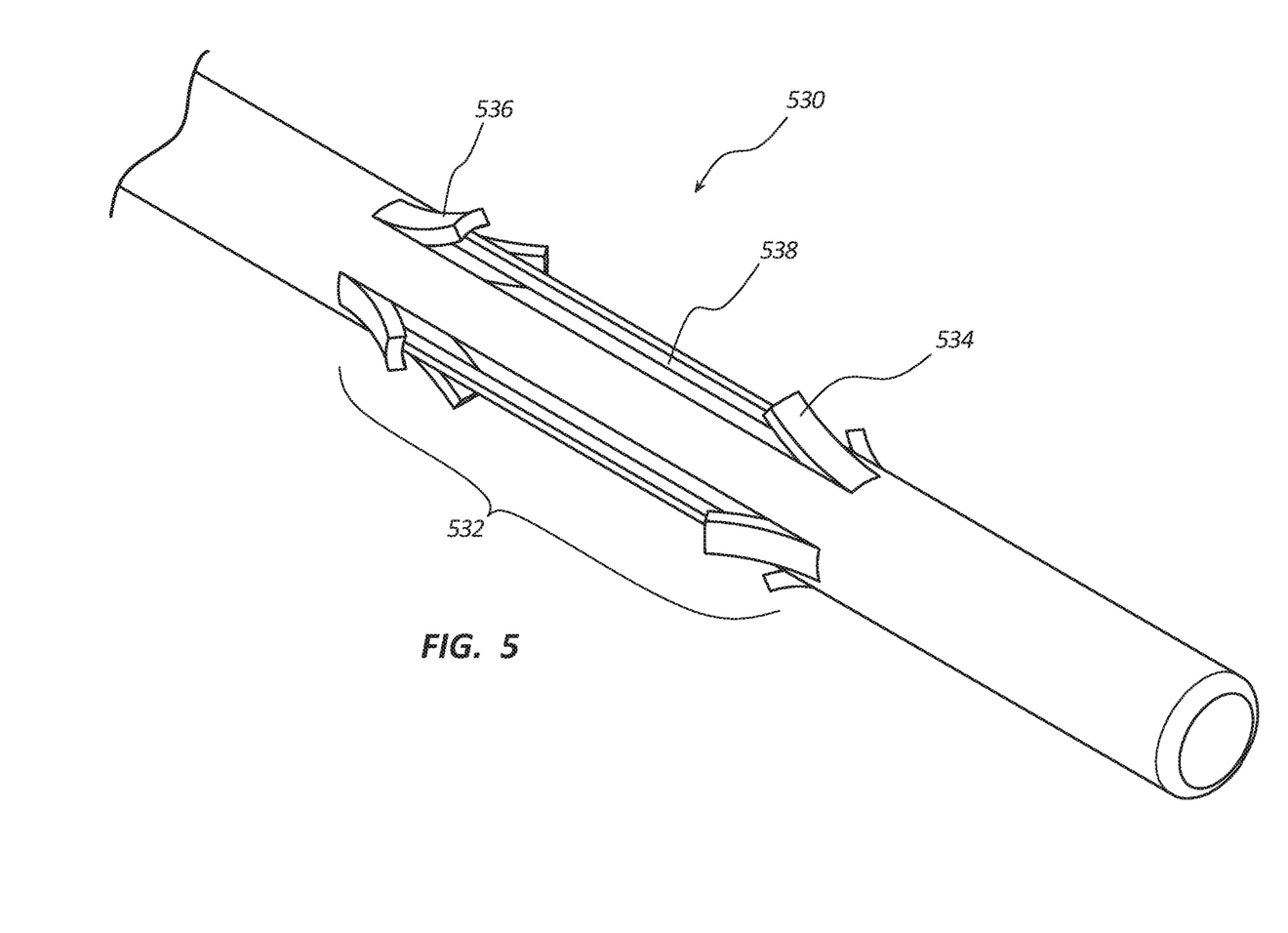
FIG. 5 is detail view of a locking mechanism of a locking stylet, according to a third embodiment.

FIG. 5 is detail view of a locking mechanism 532 of a locking stylet 530, according to a third embodiment. The locking mechanism 532 comprises a plurality of barbs (i.e., first set of barbs 534 and second set of barbs 536) to engage an inner surface of the catheter when the locking stylet 530 is inserted into a proximal opening of the catheter. The barbs 534, 536 may also be referred to as push-in fingers.

In the illustrated embodiment, the shaft is hollow and the barbs 534, 536 comprise strips cut from the distal portion of the locking stylet 530. The barbs 534, 536 are bent outward from the locking stylet 530 and remain coupled to the locking stylet 530 along one edge. Each of the first set of barbs 534 remains attached to the locking stylet 530 along an edge of the barb closest to the distal end of the locking stylet 530. Each of the second set of barbs 536 remains attached to the locking stylet 530 along an edge of the barb closest to the proximal end of the locking stylet 530. The space between the first set of barbs 534 and the second set of barbs 536 may be left as an open slot 538.

The first set of barbs 534 is positioned around the distal portion of the locking stylet 530 nearer the distal end than the second set of barbs 536. Each barb of the first set of barbs 534 extends proximally and away from a center of the locking stylet 530. Because the first set of barbs 534 is sloped away from the distal end of the locking stylet 530, the locking mechanism 532 may be inserted into a proximal opening of the catheter without catching on an edge of the catheter.

Each barb of the first set of barbs 534 is connected to the locking stylet 530 along a single edge. Each of the plurality of barbs 434 may be able to flex inward toward the center of the locking stylet 530. When the plurality of barbs 534 are deflected inward, they may exert an outward spring force.

When the locking mechanism 532 is inserted into a proximal opening of the catheter with a longitudinal force, the inner surface of the catheter deflects the first set of barbs 534 inwardly. The first set of barbs 534 may exert an outward spring force, causing the first set of barbs 534 to engage with the inner surface of the catheter. The spring force may secure the locking mechanism 532 within the catheter.

Figure 6:
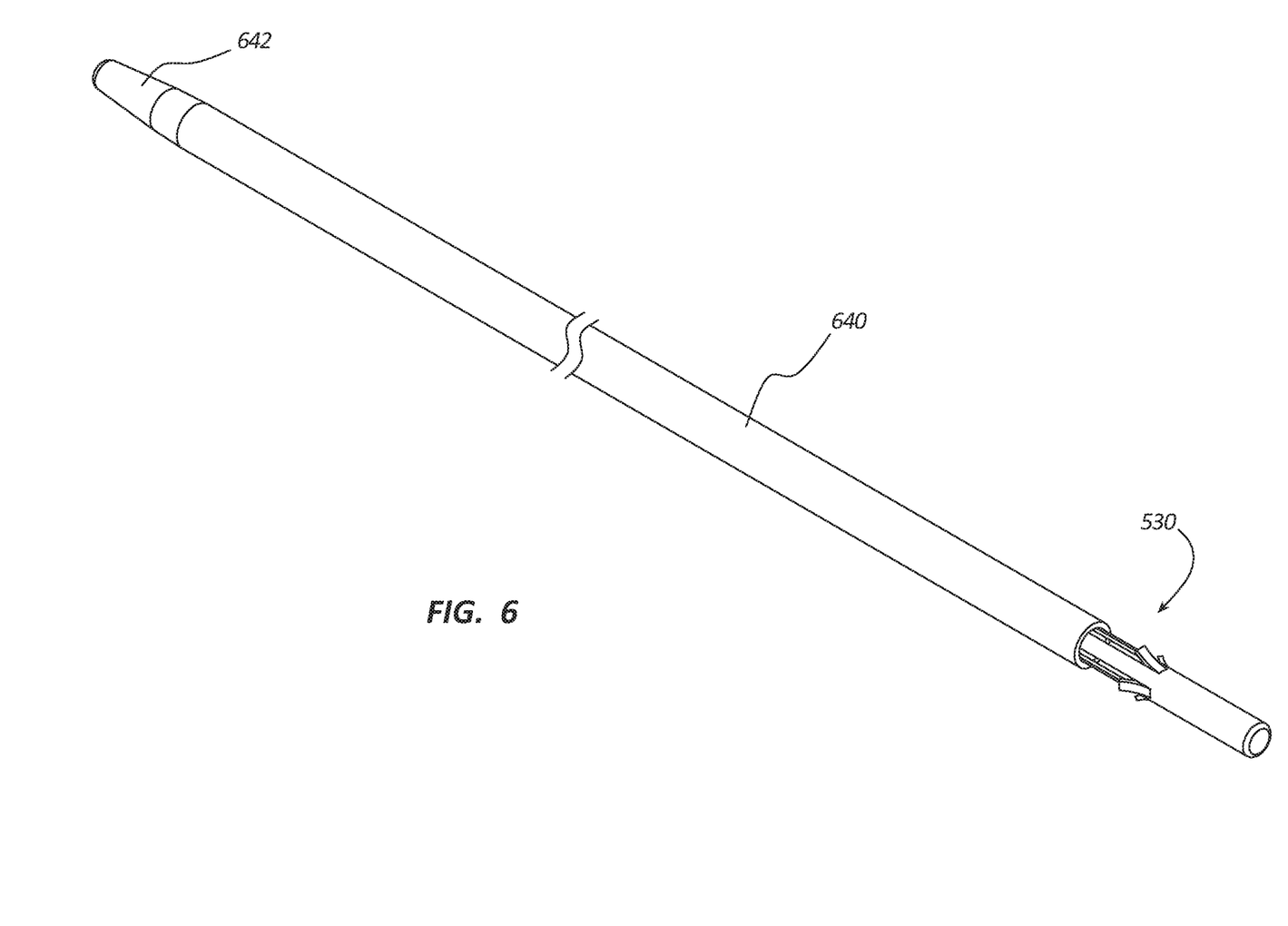
FIG. 6 is a perspective view of a locking stylet with an elongate cover, according to one embodiment.

The second set of barbs 536 is positioned around a distal portion of the locking stylet 530 nearer the proximal end than the first set of barbs 534. Each barb of the second set of barbs 536 extends distally and away from a center of the locking stylet 530. Because the second set of barbs 536 is sloped away from the proximal end of the locking stylet 530, the locking mechanism 532 may be used to secure an elongate cover to the locking stylet 530 as illustrated in FIG. 6. Additionally or alternatively, the locking mechanism 532 can stop advancement of the catheter over the locking stylet 530.

FIG. 6 is a perspective view of the locking stylet 530 of FIG. 5 with an elongate cover 640, according to one embodiment. The elongate cover 640 may comprise an extruded member and may be secured in place via a set of barbs as shown in FIG. 5. The elongate cover 640 may be flexible and surround a shaft of the locking stylet 530.

The locking stylet 530 may include a tapered proximal portion 642. As shown, the locking stylet 530 may not include a handle. Instead, in some embodiments, the locking stylet 530 may be tapered on one or both ends (e.g., tapered proximal portion 642). The tapered proximal portion 642 may allow the locking stylet 530 to be easily inserted into a sheath even if the locking stylet 530 is already secured to a catheter.

Figure 7:
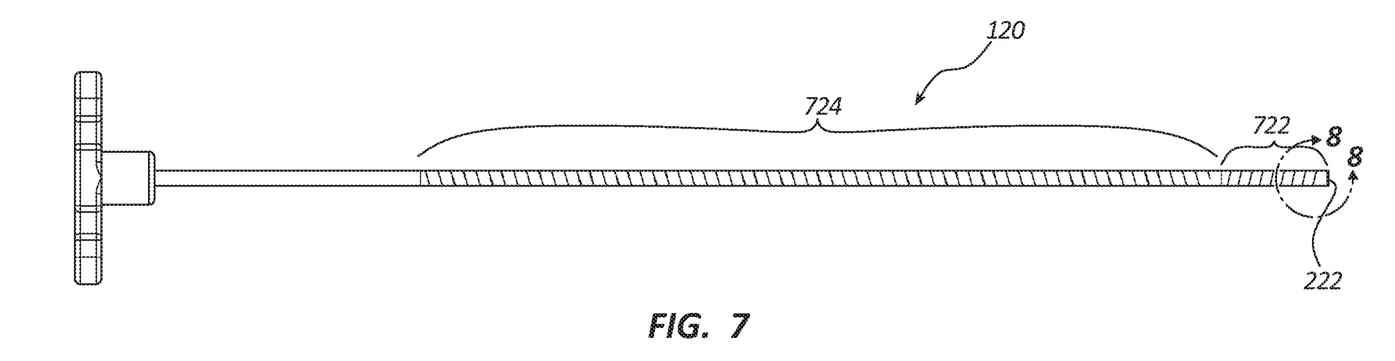
FIG. 7 is a side view of a cutting tool of the drainage catheter exchange system of FIG. 1.

FIG. 7 is a side view of a cutting tool 120 of the drainage catheter exchange system 100 of FIG. 1. The cutting tool 120 includes a hollow cannula with a cutter 222 on a distal edge.

The cutting tool 120 may be a hollow cannula and may comprise an single integral piece, such as a integral metal cannula. In the illustrated embodiment, the cutter 222 is a sharpened distal edge of a hollow cannula. In other embodiments, the cutter 222 may be separate from the cannula. For example, the cutter 222 may be embedded, glued, or otherwise coupled to the distal edge of the cannula.

In some embodiments, the cutting tool 120 includes one or more laser cut spirals along the hollow cannula. Spiral cuts, or other features may be disposed along the cutting tool 120 to increase the flexibility of the cutting tool 120 to traverse along a catheter and follow the path of the catheter. In some embodiments, one or more spiral cuts on the cutting tool 120 may have equal distance between rotations. In some embodiments, one or more spiral cuts along the cutting tool 120 may vary in pitch or density. In other words, the distance between rotations of one or more spiral cuts may vary across the length of the cutting tool 120. Variation in spiral cut density provides the cutting tool 120 with a flexibility profile that varies along a length of the cutting tool 120.

In the illustrated embodiment, the cutting tool 120 features two flexible sections (i.e., distal flexible section 722 and proximal flexible section 724). The distal flexible section 722 includes more rotations per length of the spiral cut than the proximal flexible section 724. The closer spiral cuts of the distal flexible section 722 may have a higher pitch than the further apart spiral cuts of the proximal flexible section 724. The greater density of the spiral cut along the distal flexible section 722 provides the distal flexible section 722 with a greater flexibility than the proximal flexible section 724. The greater flexibility of the distal flexible section 722 allows the tip of the cutting tool 120 to track the path of the catheter more readily. The distal flexible section 722 may be configured to track the catheter around a tight radius and may be configured to transition and lead proximal flexible section 724 over such a path. In other words, the distal flexible section 722 can guide the proximal flexible section 724 around such tight turns. After the distal flexible section 722 follows a radius the rest of the cannula will follow even if the rest of cannula may distort that radius (or tend to straighten the catheter). Further, the cutting tool 120 may be configured such that the distal flexible section 722 is configured to be disposed over more tortuous curvature than other portions of the cutting tool 120.

In the illustrated embodiment, the distal flexible section 722 features a first spiral cut and the proximal flexible section 724 features a second spiral cut. The first spiral cut has a pitch in the opposite direction of the second spiral cut. In some embodiments, the two spiral cuts are joined. In other embodiments, the spiral cuts are discrete. In some embodiments, the pitch of the spiral cuts may be in the same direction.

In some embodiments, the one or more spiral cuts may be cut uniformly to create a flexibility profile of the cutting tool 120 with the same flexibility throughout.

In some embodiments, the cutting tool 120 may feature three or more sections with varying flexibility.

In some embodiments, the density of the one or more spiral cuts may gradually change from one end of the cutting tool 120 to another end of the cutting tool 120. For example, the spiral cut may be dense at a distal portion of the cutting tool and gradually the rotations of the cutting tool 120 may widen as the spiral cut approaches a proximal portion of the cutting tool 120.

Figure 8:
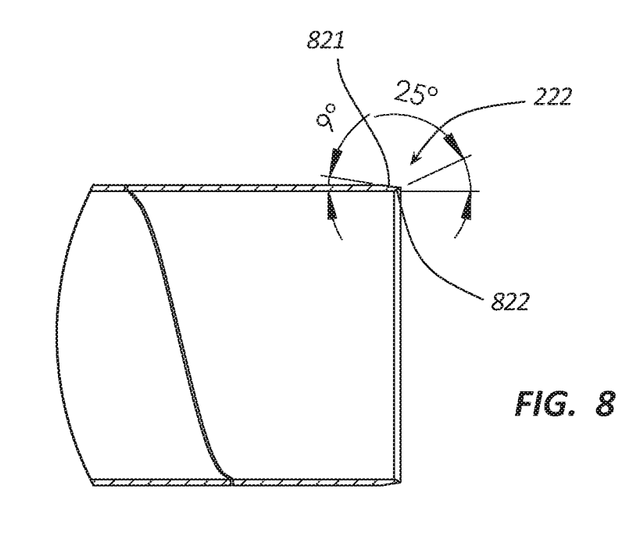
FIG. 8 is a cross-sectional view of a distal portion of distal portion of the cutting tool of FIG. 7.

FIG. 8 is a cross-sectional view of a distal portion of the cutter 222 of FIG. 7. As shown, the cutter 222 includes a first bevel 821 extending from the outer diameter of the cutting tool sidewall to the inner diameter of the cutting tool sidewall, and a second bevel 822 extending from the inner diameter of the cutting tool sidewall to the outer diameter of the cutting tool sidewall. The angles shown on FIG. 8 are exemplary and may be changed to any suitable angle. The first bevel 821 and the second bevel 822 meet at a vertex that forms the sharpened edge of the cutter 222. The vertex is in between the outer diameter of the cutting tool sidewall and the inner diameter of the cutting tool sidewall to avoid damaging a sheath outside of the cutter 222 or a catheter inside the cutter 222. In other words, the first bevel 821 may displace the cutting edge away from an outer sheath and the second bevel 822 may displace the cutting edge away from the catheter, to reduce or avoid skiving of the catheter and the cutter 222 is advanced along the catheter.

Figure 9A:
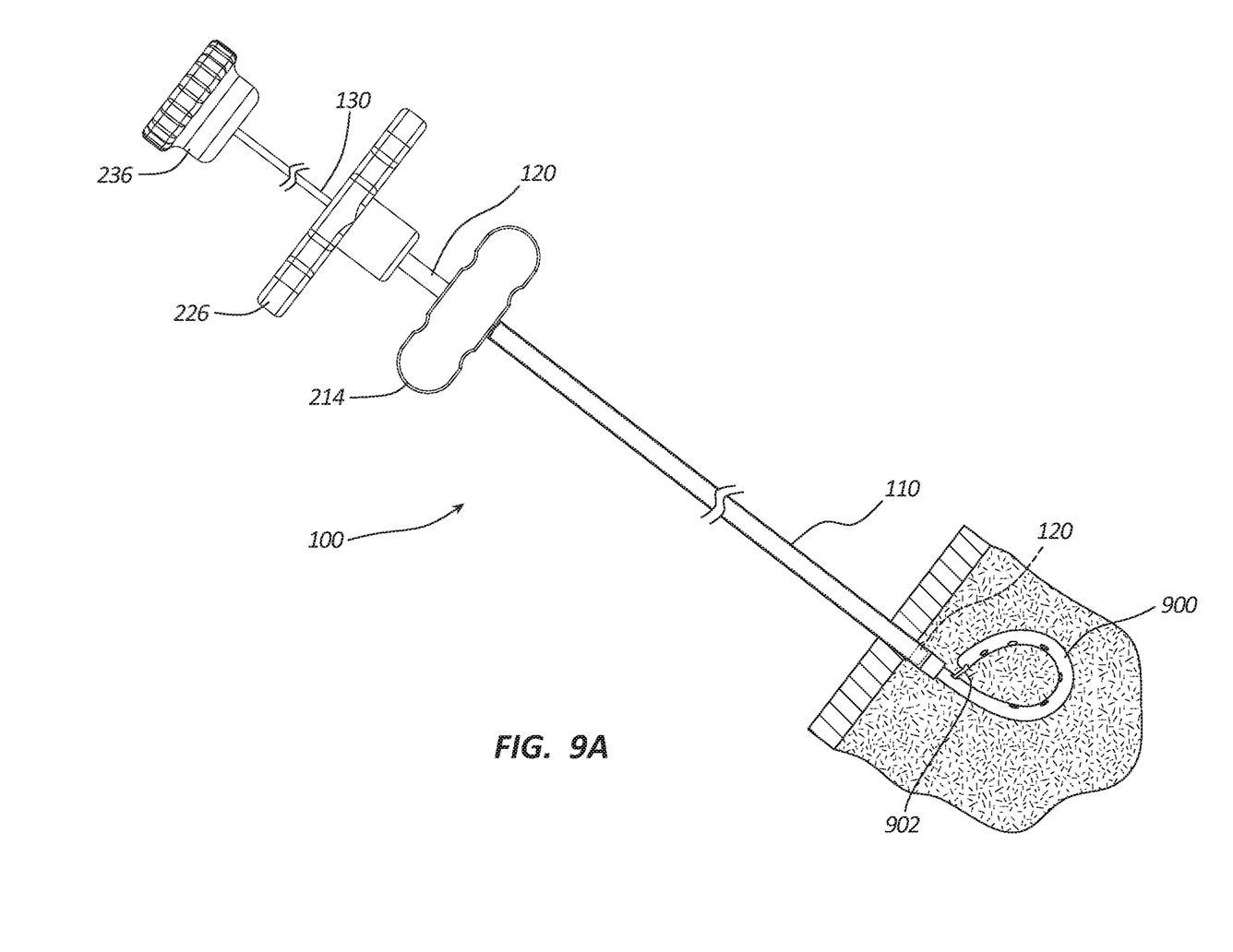
FIG. 9A is a schematic representation of the drainage catheter exchange system of FIG. 1 being inserted into a patient to remove a drainage catheter.
Figure 9B:
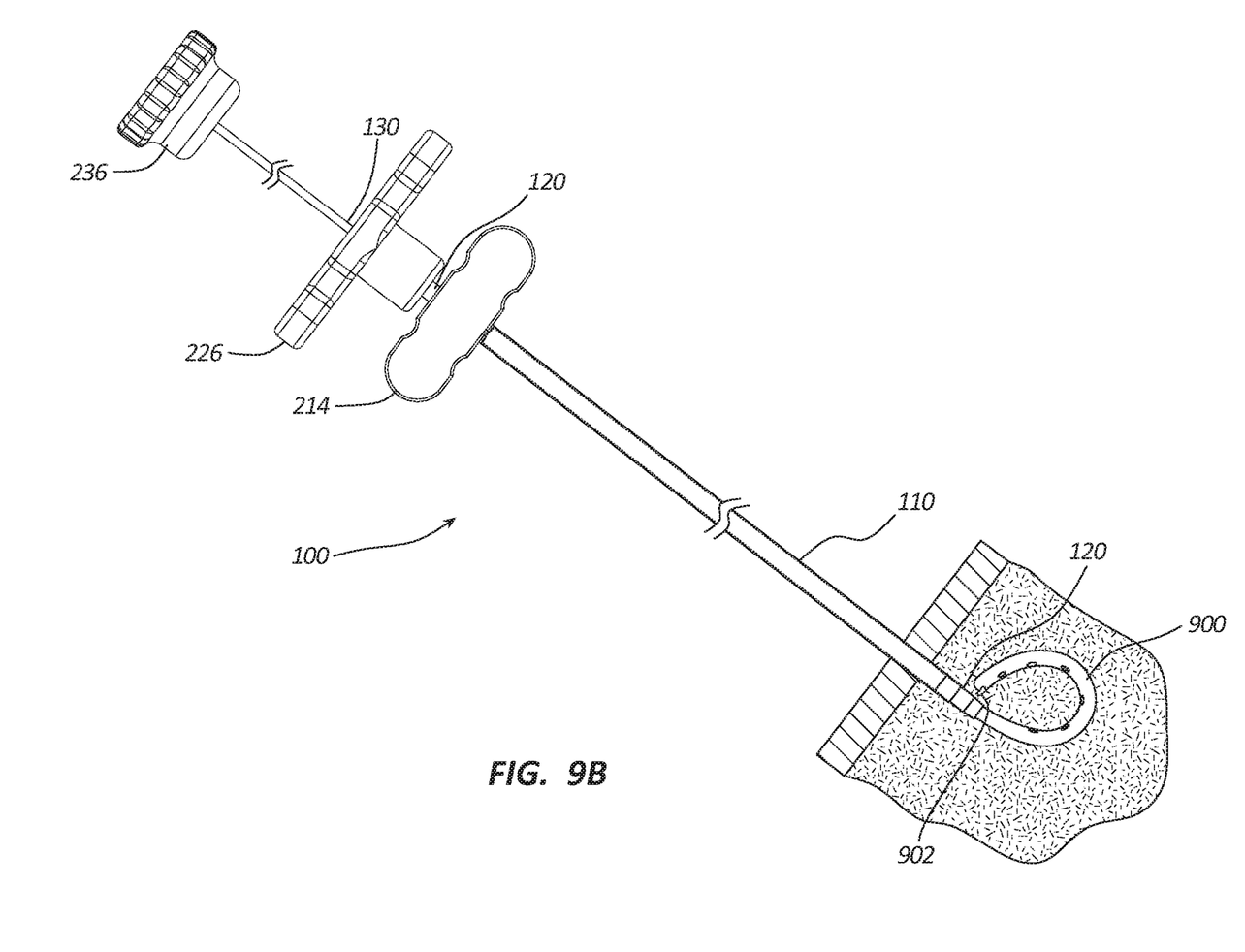
FIG. 9B is a schematic representation of the drainage catheter exchange system of FIG. 1 severing a suture of a drainage catheter.

FIGS. 9A and 9B illustrate the drainage catheter exchange system 100 of FIG. 1 in use. Specifically, FIG. 9A is a schematic representation of the drainage catheter exchange system 100 of FIG. 1 being inserted into a patient to remove a drainage catheter 900. FIG. 9B is a schematic representation of the drainage catheter exchange system 100 of FIG. 1 severing a suture 902 of the drainage catheter 900. The drainage catheter exchange system 100 may facilitate removal of the drainage catheter 900 even when the suture 902 has become encrusted.

As shown in FIG. 9A, in some procedures, the sheath 110 and the cutting tool 120 are inserted into a patient over a previously placed drainage catheter 900. To prevent the drainage catheter 900 from moving as the sheath 110 and the cutting tool 120 move along the drainage catheter 900, the locking stylet 130 may couple to the proximal end of the drainage catheter 900. A physician may hold onto a shaft of the drainage catheter 900 or a handle of the drainage catheter 900 to limit movement of the drainage catheter 900. In some instances, practitioner may cut or otherwise remove a hub from the drainage catheter 900 to facilitate advancing the sheath 100 over the drainage catheter 900 and to facilitate coupling of the locking stylet 130 to the drainage catheter.

The physician advances the sheath 110 and the cutting tool 120 along the drainage catheter 900 to near the suture 902. The physician may apply a longitudinal force to the handle 214 of the sheath 110 and the handle 226 of the cutting tool 120 to advance the sheath 110 and the cutting tool 120. The physician may track the position of the sheath 110 and the cutting tool 120 relative to the suture 902 using fluoroscopy, ultrasound, or measurement.

As shown in FIG. 9B, the cutting tool 120 may be advanced from the sheath 110 to sever the suture 902. The physician may withdraw the drainage catheter 900 by pulling the locking stylet 130 away from the sheath 110 and the handle 226. The physician may also remove the cutting tool 120 and leave the sheath 110 in the patient to serve as an introducer for a new drainage catheter. In some embodiments, the sheath 110 is splittable, so that once the new drainage catheter is in place, the physician may split the sheath 110 to remove it from the patient if the new drainage catheter comprises a hub.

Figure 10:
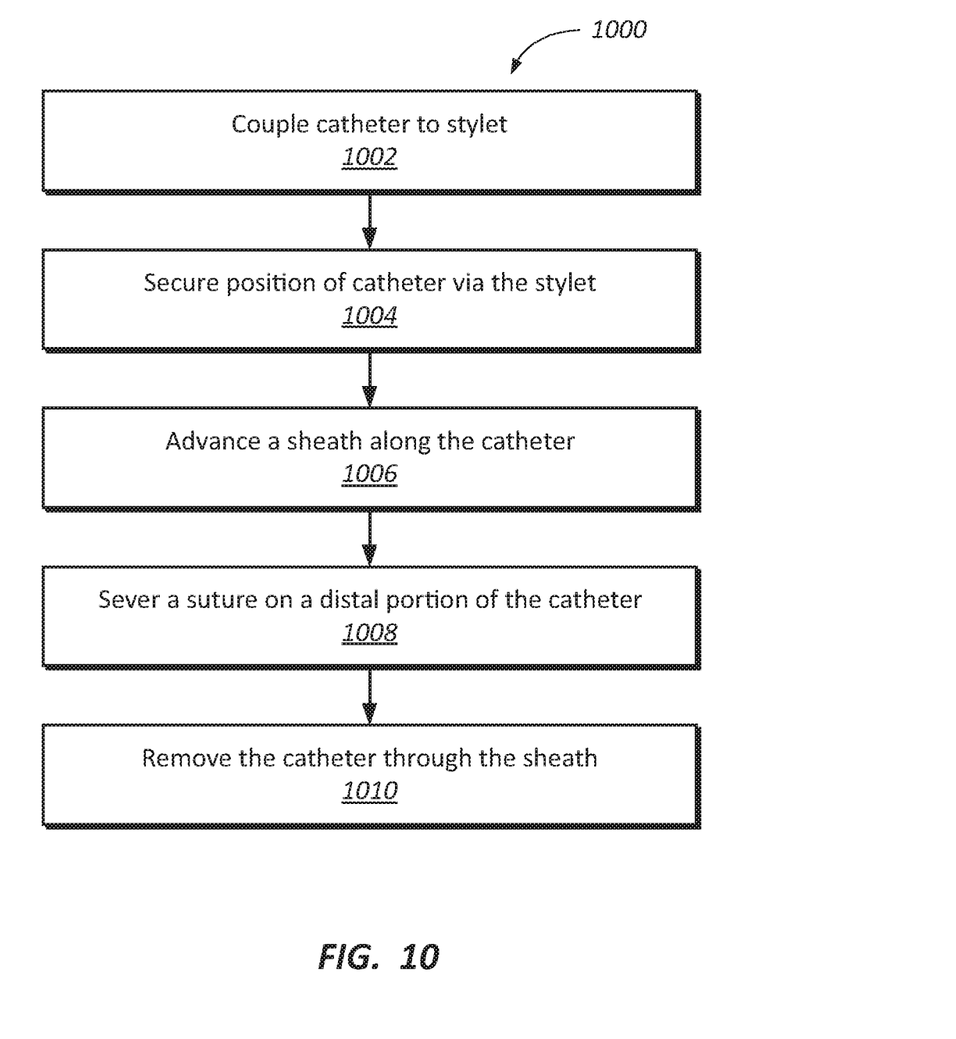
FIG. 10 is a flow chart of a method for removing a catheter using a drainage catheter exchange system, according to one embodiment.

FIG. 10 is a flow chart of a method 1000 for removing a catheter using a drainage catheter exchange system. The method includes coupling 1002 the catheter to a stylet. The stylet includes a shaft and a locking mechanism at a distal portion of the shaft. The locking mechanism may be any of the locking mechanisms described herein or any other suitable securement means. To couple 1002 the catheter and the stylet, a physician may remove a hub of the catheter and couple the locking mechanism to the distal portion of the shaft to a proximal portion of a catheter. The physician may secure 1004 the position of the catheter via the shaft of the stylet by holding the stylet in place. The physician may advance 1006 a sheath along a length of the catheter and sever 1008 a suture on a distal portion of the catheter. The physician may remove 1010 the catheter through the sheath by pulling on the locking stylet.

In some embodiments, severing 1008 the suture comprises applying a force to the suture via the sheath.

In some embodiments, severing 1008 the suture comprises extending a cutting tool beyond the sheath.

In some embodiments, the method may further comprise placing a new catheter through the sheath, and removing the sheath and the cutter. The sheath may be removed by splitting the sheath away from a hub of the new catheter.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Changes may be made to the details of the above-described embodiments without departing from the underlying principles of the present disclosure.

The invention claimed is:

1. A catheter exchange system comprising:
    a cannula, the cannula comprising a flexible shaft and a cutter at a distal end of the flexible shaft;
    a sheath positioned around at least a portion of the cannula; and a stylet comprising:
        a shaft; and
        a locking mechanism at a distal portion of the shaft, wherein the locking mechanism comprises one or more barbs formed in a wall of the shaft, wherein the one or more barbs are biased outward from the shaft,
    wherein the cutter may selectively transition between a first position in which the cutter is within the sheath and a second position in which the cutter is extended beyond the sheath,
    wherein the one or more barbs includes a first set of barbs and a second set of barbs, and
    wherein the first set of barbs are oriented distally and the second set of barbs are oriented proximally.

2. The system of claim 1, wherein the cutter comprises a circular cutting blade.

3. The system of claim 2, wherein the circular cutting blade is a sharpened edge around a circumference of the distal end of the flexible shaft.

4. The system of claim 2, wherein the cutter comprises a series of serrations.

5. The system of claim 1, wherein the sheath is splittable.

6. The system of claim 1, wherein the one or more barbs are configured to engage an inner surface of a catheter when the shaft is inserted into a proximal opening of the catheter.

7. The system of claim 1, wherein the cannula includes one or more spiral cuts along a length.

8. The system of claim 7, wherein a distance between rotations of the one or more spiral cuts is less at a distal portion of the cannula than the distance between rotations of the one or more spiral cuts at a proximal portion.

9. The system of claim 1, further comprising a pig-tail catheter configured to be disposed within a patient with a distal portion of the pig-tail curved back toward and sutured to the pig-tail catheter, wherein the cannula is configured to surround a proximal portion of the pig-tail catheter,
    and wherein the one or more barbs engage an inner surface of the pig-tail catheter when the shaft is inserted into a proximal opening of the catheter.

10. A stylet comprising:
    a shaft;
    a locking mechanism at a distal portion of the shaft, wherein the locking mechanism couples the distal portion of the shaft to a proximal portion of a catheter; and
    a handle at a proximal end of the shaft,
    wherein a width of the handle is greater than a diameter of the shaft,
    wherein the locking mechanism comprises one or more barbs formed in a wall of the shaft, wherein the one or more barbs are biased outward from the shaft, wherein the one or more barbs are configured to engage an inner surface of the catheter when the shaft is inserted into a proximal opening of the catheter,
    wherein the one or more barbs includes a first set of barbs and a second set of barbs, and
    wherein the first set of barbs are oriented distally and the second set of barbs are oriented proximally.

11. The stylet of claim 10, wherein the locking mechanism comprises a helical thread around a conical tip, wherein the helical thread is configured to engage an inner surface of the catheter when the conical tip is inserted into a proximal opening of the catheter and rotated.

12. The stylet of claim 10, wherein the handle comprise a circular grip with a diameter greater than the diameter of the shaft.

* * * * *